(12) United States Patent
Patel et al.

(10) Patent No.: US 12,352,759 B2
(45) Date of Patent: Jul. 8, 2025

(54) ASSAY METHOD OF ANTIBODY

(71) Applicant: Kashiv BioSciences, LLC, Piscataway, NJ (US)

(72) Inventors: Rajeshwari Patel, Ahmedabad (IN); Praveen Kumar Anidil Kizhakinagath, Ahmedabad (IN)

(73) Assignee: Kashiv BioSciences, LLC, Piscataway, NJ (US)

( * ) Notice: Subject to any disclaimer, the term of this patent is extended or adjusted under 35 U.S.C. 154(b) by 0 days.

(21) Appl. No.: 18/769,708

(22) Filed: Jul. 11, 2024

(65) Prior Publication Data
US 2025/0003984 A1    Jan. 2, 2025

Related U.S. Application Data

(63) Continuation of application No. PCT/IB2023/056773, filed on Jun. 29, 2023.

(30) Foreign Application Priority Data

Jun. 29, 2022  (IN) .............................. 202221037354

(51) Int. Cl.
G01N 33/53     (2006.01)
C12Q 1/40      (2006.01)
G01N 33/68     (2006.01)

(52) U.S. Cl.
CPC ........... *G01N 33/6854* (2013.01); *C12Q 1/40* (2013.01); *G01N 2333/70535* (2013.01); *G01N 2333/765* (2013.01); *G01N 2333/924* (2013.01)

(58) Field of Classification Search
None
See application file for complete search history.

(56) References Cited

U.S. PATENT DOCUMENTS

| | | | |
|---|---|---|---|
| 5,994,511 A | 11/1999 | Lowman et al. | |
| 2002/0187520 A1 | 12/2002 | Helm et al. | |
| 2010/0297177 A1* | 11/2010 | Buening | A61P 31/18 435/235.1 |
| 2020/0325248 A1 | 10/2020 | Chen et al. | |

FOREIGN PATENT DOCUMENTS

WO    WO-2022/039547 A1    2/2022

OTHER PUBLICATIONS

Merchand et al., Human serum IgE-mediated mast cell degranulation shows poor correlation to allergen-specific IgE content, Allergy, 2003; 58, pp. 1037-1043. (Year: 2003).*
Guo et al., A robust and stable reporter gene bioassay for anti-IgE antibodies, Analytical and Bioanalytical Chemistry, 2020, 412, pp. 1901-1914. (Year: 2020).*
Dibbern et al., (RBL cells expressing human FceRI are a sensitive tool for exploring functional IgE-allergen interactions: studies with sera from peanut-sensitive patients, Journal of Immunological Methods 274; 2003, pp. 37-45. (Year: 2003).*
International Search Report and Written Opinion for PCT/IB2023/056773 mailed on Nov. 15, 2023 (7 pages).

* cited by examiner

*Primary Examiner* — Gary Counts
(74) *Attorney, Agent, or Firm* — Goodwin Procter LLP

(57) ABSTRACT

Disclosed is a method of for analyzing the relative potency of an antibody of interest using β-hexosaminidase degranulation in human cell line. This improved assay method is used to characterize functional assay of anti-IgE antibody with B-hexosaminidase.

19 Claims, 5 Drawing Sheets

ASSAY METHOD OF ANTIBODY

CROSS-REFERENCE TO RELATED APPLICATIONS

This application is a Continuation of International Application No. PCT/IB2023/056773, filed on Jun. 29, 2023, which claims the benefit of and priority to Indian Patent Application No. 202221037354, filed on Jun. 29, 2022, each of which is incorporated by reference herein in its entirety.

FIELD OF THE INVENTION

The present invention relates to an assay method for determining the relative bioactivity or potency of antibody of interest using β-hexosaminidase degranulation in human cell line. The present invention relates to characterization of functional assay of anti-IgE antibody with B-hexosaminidase.

BACKGROUND OF THE INVENTION

Every area of the biomedical science is in need of a system to assay chemical and biochemical reactions and determine the presence and quantity of particular analyte. Numerous methodologies have been developed over the years to meet the demands of these fields. In general, limitations exist in the areas of specificity and sensitivity of most assay system.

Biological activity is a critical quality attribute for biopharmaceuticals, which is accurately measured using an appropriate relative potency bioassay. Developing a bioassay is a complex, rigorous undertaking that needs to address several challenges including modelling all the mechanisms of action associated with the biotherapeutic.

Omalizumab is a recombinant, humanized anti IgE monoclonal antibody which binds and neutralizes free IgE and thus reduces the availability of IgE for binding to cellular receptors. The bioactivity of Omalizumab is critical quality attribute and hence requires a mechanism of action based functional bioassay to be developed and used for analysis of these samples.

The mode of action-based bioassay is better, not only to gain greater process and product understanding but also to gain a better understanding of method performance prior to mimicking the actual function in vivo.

Design strategies for bioassays are driven by the drugs intended physiological mechanism of action. A well-designed bioassay will accurately capture the biological activity of a drug candidate.

B-hexosaminidase is a lysosomal enzyme released by mast cells and basophils and are known to be in-vitro activation markers of these cells. The enzyme is released from the preformed granules in the cellular cytoplasm long with other proteins such as histamine, up on activation. Hence, B-hexosaminidase has been used a biomarker for the present assay.

U.S. Pat. No. 5,994,511 discloses assay method developed for determining the potency of antibody by releasing histamine which requires long incubation period (twice time) about 24 hours post seeding. In addition, prior art process involved additional washing step, centrifugation and incubation that makes the entire assay method lengthy (more than 50 hours) and cumbersome. We also noticed that the prior art process even doesn't provide desire result of assay. However, the present invention provides a simple, effective, robust, and short assay method which is completed in lesser time and provides superior assay result.

The overall assay duration has been brought down to less than 2 days in the present invention in comparison to 4 days of assay procedure disclosed in prior art. The present invention provides superior and improved assay method which is evident of FIG. 2 of present invention which is improved over the teaching of U.S. Pat. No. 5,994,511 shown in FIG. 5.

The objective of present invention is to describe the method of analysis for estimation of relative potency of Omalizumab using β-hexosaminidase degranulation assay in human FcRIU expressing RBL-2H3 cell line. The present invention is giving comparison between histamine release mechanism and β-hexosaminidase degranulation assay with similar potency.

The objective of the present invention is to minimize the seeding time by 4-5 hours compared to already known histamine release functional assay.

It has been noted that β-hexosaminidase degranulation assay is cost effective assay, more precise, accurate and reduce time during performing assay method.

SUMMARY OF THE INVENTION

In an embodiment, the present invention provides an improved assay method comprising:
 a) sensitising of RBL 2H3 cell comprising hFCεRIa receptor with IgE or anti NP IgE and neutralizing the suitable concentration of anti-IgE antibody by incubating at suitable temperature for suitable time;
 b) transferring the suitable concentration of sensitized and neutralized mixture of anti-IgE antibody and anti NP-IgE to pre-seeded assay plate;
 c) incubating the pre-seeded plate for suitable time at suitable temperature;
 d) washing the pre-seeded assay plate;
 e) mixing the suitable antigen into pre-seeded assay plate and incubating for at least 2 hours, preferably 70 minutes;
 f) transferring the supernatant from the pre-seeded assay plate into test assay plate;
 g) incorporating the suitable substrate into test assay plate and incubate for suitable time;
 h) determining the bioactivity of anti-IgE antibody.

In an embodiment, the present invention provides an improved assay method to determine the bioactivity or efficacy of an anti-IgE antibody comprising:
 a) seeding cells in the assay plate with suitable media to form cell suspension;
 b) incubating the cell suspension with $CO_2$ at suitable physiological temperature for suitable time;
 c) sensitising and neutralizing the antibody of interest and anti NP-IgE simultaneously and incubating the antibody of interest and anti NP-IgE mixture less than 24 hours;
 d) transferring the antibody of interest and anti NP-IgE mixture to the seeded assay plate to form assay mixture;
 e) incubating the assay mixture at suitable physiological temperature for suitable time;
 f) washing the assay mixture with suitable assay buffer;
 g) incubating the assay mixture with antigen at suitable physiological temperature for not more than 2 hours, preferably 70 min;
 h) treating the supernatant with suitable substrate in assay plate;

i) measuring the efficacy of the antibody of interest.

In an embodiment, the present invention provides an improved assay method to determine the bioactivity of an antibody comprising:
a) seeding cells in the assay plate with suitable media to form cell suspension;
b) incubating the cell suspension with $CO_2$ at suitable physiological temperature for suitable time 4 to 5 hours;
c) sensitising and neutralizing the antibody of interest and anti NP-IgE in seeded cell plate incubating the antibody of interest and anti NP-IgE mixture in seeded cell plate for less than 24 hours at suitable physiological temperature to form antibody NP-IgE complex;
d) washing the first assay mixture with suitable assay buffer to form second assay mixture;
e) incubating the second assay mixture with suitable amount of NP-BSA (bovine serum albumin) for not more than 2 hours, preferably 70 min with $CO_2$ at suitable physiological temperature to form third assay mixture;
f) treating the third assay mixture or supernatant derived from it with suitable substrate in assay plate to form fourth assay mixture;
g) incubating the fourth assay mixture with $CO_2$ at suitable physiological temperature for suitable time;
h) reading the plate to measure the efficacy of the antibody of interest wherein the antibody of interest and anti NP-IgE is incubated for at least 18-24 hours hours to form neutralised complex of antibody of interest and anti NP-IgE before performing mixing in step (c); wherein the assay provides the less variation in histamine and B-hex.

In an embodiment, the invention represents an improved assay method to determine the efficacy of an antibody the assay method comprising:
a) mixing the allergen-antibody and antibody of interest in the assay plate seeded with suitable cell;
b) incubating the assay plate with $CO_2$ at suitable physiological temperature for suitable time;
c) washing the assay plate with suitable assay buffer;
d) stimulating the suitable cell with suitable stimulator;
e) optionally incubate the assay plate for suitable time;
f) adding the suitable substrate in the assay plate;
g) optionally incubate the assay plate for suitable time;
h) reading the plate to determine efficacy of the antibody of interest.

In an embodiment, the invention represents an improved assay method to determine the efficacy of an antibody the assay method comprising:
a) mixing the allergen-antibody and antibody of interest in the assay plate seeded with suitable cell;
b) incubating the assay plate with $CO_2$ at suitable physiological temperature for suitable time;
c) washing the assay plate with suitable assay buffer;
d) stimulating the suitable cell with suitable stimulator;
e) optionally incubate the assay plate for suitable time;
f) extracting the supernatant from the assay plate;
g) reacting the extracted supernatant with suitable substrate in the assay plate;
h) optionally incubate the assay plate for suitable time;
i) reading the plate to determine efficacy of the antibody of interest.

In an embodiment, the invention represents an improved assay method to determine the efficacy of an antibody the assay method comprising:
a) seeding cells in the assay plate with suitable media to form cell suspension;
b) incubating the cell suspension with $CO_2$ at suitable physiological temperature for suitable time;
c) mixing the antibody of interest and anti NP-IgE in seeded cell plate;
d) incubating the antibody of interest and anti NP-IgE mixture at suitable physiological temperature for suitable time to form antibody NP-IgE complex;
e) perform washing the first assay mixture with suitable assay buffer to form second assay mixture;
f) incubating the second assay mixture with suitable amount of NP-BSA (bovine serum albumin) with $CO_2$ at suitable physiological temperature for suitable time to form third assay mixture;
g) treating the third assay mixture or supernatant derived from it with suitable substrate in assay plate;
h) incubating the fourth assay mixture with $CO_2$ at suitable physiological temperature for suitable time;
i) reading the plate to measure the efficacy of the antibody of interest.

In an embodiment, the invention represents an improved assay method to determine the efficacy of an antibody the assay method comprising:
a) seeding cells in the assay plate with suitable media to form cell suspension;
b) incubating the cell suspension with $CO_2$ at suitable physiological temperature for suitable time;
c) incubating the antibody of interest and anti NP-IgE mixture at suitable physiological temperature for suitable time to form antibody NP-IgE complex;
d) mixing the antibody NP-IgE complex into seeded assay plate to form first assay mixture;
e) incubating the first assay mixture with $CO_2$ at suitable physiological temperature for suitable time;
f) perform washing the first assay mixture with suitable assay buffer to form second assay mixture;
g) incubating the second assay mixture with suitable amount of NP-BSA (bovine serum albumin) with $CO_2$ at suitable physiological temperature for suitable time to form third assay mixture;
h) treating the third assay mixture or supernatant derived from it with suitable substrate in assay plate;
i) incubating the fourth assay mixture with $CO_2$ at suitable physiological temperature for suitable time;
j) reading the plate to measure the efficacy of the antibody of interest.

In an embodiment, the invention represents an improved assay method to determine the efficacy of an antibody the assay method comprising:
a) seeding RBL-2H3 hFcεR1A cells in the assay plate with MEM media to form cell suspension;
b) incubating the cell suspension with 5% $CO_2$ at 37° C. for 4 hours to 5 hours;
c) incubating the antibody of interest and anti NP-IgE mixture at 37° C. for 1.5 hour to 2 hours to form antibody NP-IgE complex;
d) mixing the antibody NP-IgE complex into seeded assay plate to form first assay mixture;
e) incubating the first assay mixture with 5% $CO_2$ at 37° C. for 18 hours to 24 hours;
f) perform washing twice of first assay mixture with suitable amount Tyrode's buffer containing 1% BSA to form second assay mixture;

g) incubating the second assay mixture with suitable amount of NP-BSA (bovine serum albumin) with 5% $CO_2$ at 37° C. for 60 minutes to form third assay mixture;

h) treating the third assay mixture or supernatant derived from it with M-NAG substrate in assay plate;

i) incubating the fourth assay mixture with $CO_2$ at 37° C. for 30 minutes to 40 minutes;

j) reading the plate to measure the efficacy of the antibody of interest.

In an embodiment, the present invention provides a shorter period of assay method and superior result over known art.

DETAIL DESCRIPTION OF THE INVENTION

Figure 1:
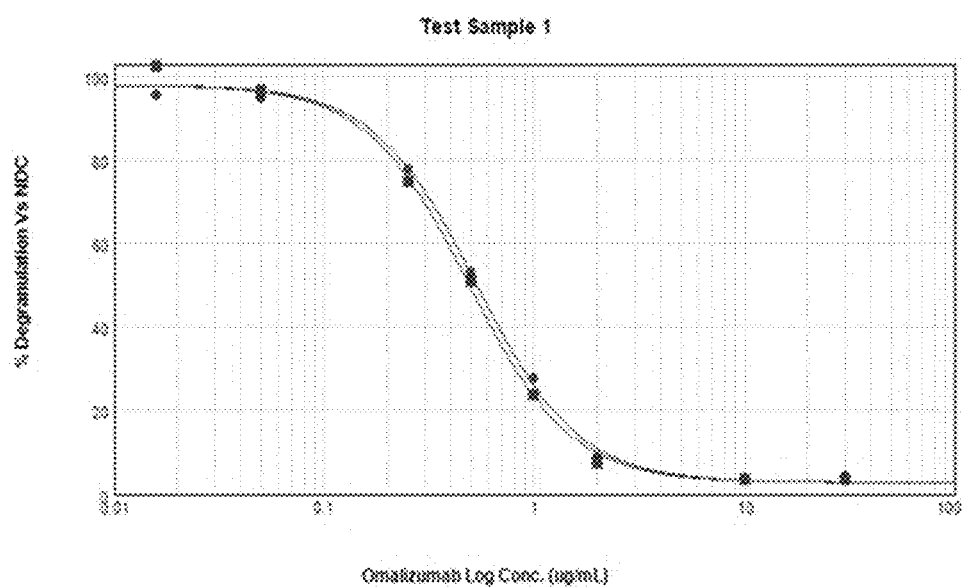
FIG. 1: Representative graph of Degranulation assay
Figure 2:
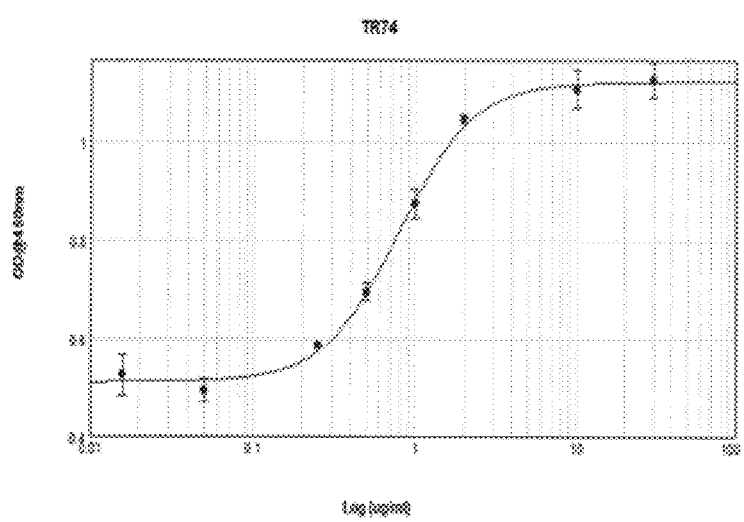
FIG. 2: Representative graph of Histamine assay (Dose dependent inhibition of Histamine release)
Figure 3:
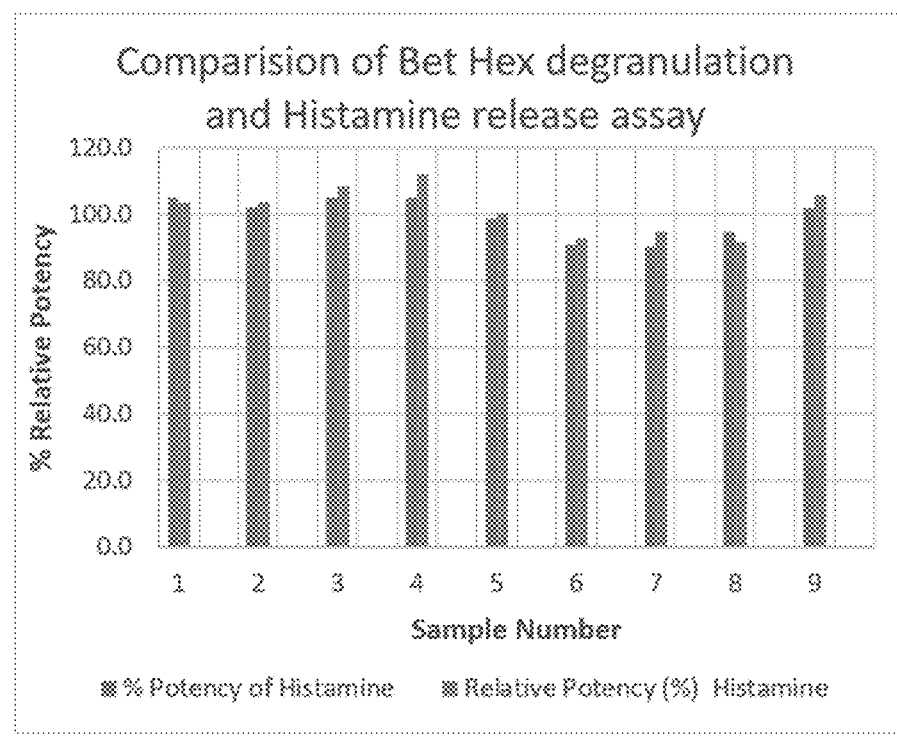
FIG. 3: Comparison of Bet Hex degranulation and Histamine release assay

The present invention provides non availability or reduced availability of IgE to FcεRI cell membrane receptors results in fewer episodes of airway inflammation, asthma symptoms and exacerbations in patients with severe allergic asthma. Unless otherwise indicated, terms in this specification are intended to have their ordinary meaning in the relevant art.

The present invention related to measurement of bioactivity of anti-IgE monoclonal antibody. Further, the present invention provides mechanism of action based functional bioassay to determine the bioactivity of anti-IgE monoclonal antibody.

In the present invention, a human specific IgE generated against 4-hydroxy-3-nitrophenylacetyl (NP) is pre incubated with Omalizumab and then introduced to the pre seeded cells. Binding of Omalizumab to anti-NP IgE make IgE less available for binding and sensitizing of cellular receptors. The released β-hexosaminidase is detected by an enzymatic reaction using 4-methylumbelliferyl-Nacetyl-β-D-glucosamine (M-NAG) as a substrate which when acted upon by β-hexosaminidase, releases fluorescent 4-methylumbelliferone in acidic citric acid buffer which is measured using a multi-mode plate reader after stopping the reaction with alkaline sodium carbonate buffer.

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. There are only two types of light chain: A and K. In humans they are similar, but only one type is present in each antibody. Heavy chains are classified as mu, delta, gamma, alpha, or epsilon, and define the antibody's isotype as IgM, IgD, IgG, IgA, and IgE, respectively.

Anti-IgE antibodies of the present disclosure specifically bind to an immunoglobulin E (IgE) polypeptide. In certain embodiment, the antibody specifically binds to "circulating" or "free" IgE and also to receptor bound IgE. For example, in certain aspects, the anti-IgE antibody specifically binds to IgE regardless of whether the IgE is bound to the high affinity IgE receptor.

The term "Antibody fragments", as used herein, is a portion of a full-length antibody, generally the antigen binding or variable region thereof. Examples of antibody fragments include Fab, Fab', F(ab')2, and Fv fragments; diabodies; linear antibodies; single-chain antibody molecules; and multispecific antibodies formed from antibody fragments.

The term "Fab", as used herein, is fragment contains a variable and constant domain of the light chain and a variable domain and the first constant domain (CH1) of the heavy chain. F(ab)'2 antibody fragments comprise a pair of Fab fragments that are generally covalently linked near their carboxy termini by hinge cysteines.

The term "Fv", as used herein, is the minimum antibody fragment which contains a complete antigen-recognition and binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

The term "monoclonal antibody", as used herein, is refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences "Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit, or nonhuman primate having the desired specificity, affinity, and capacity. The term "human antibody", as used herein, is one which possesses an amino acid sequence which corresponds to that of an antibody produced by a human and/or has been made using any of the known techniques for making human antibodies. This definition of a human antibody specifically excludes a humanized antibody comprising non-human antigen-binding residues.

The term "Fc region", as used herein, is to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The term "Binding" or "specific binding", as used herein, generally refers to binding between two molecules (such as between an antibody and one or more targets, an anti-IgE antibody and an IgE, and an anti-drug antibody and the drug) with sufficient affinity.

The term "Binding affinity", as used herein, generally refers to the strength of the sum total of monovalent interactions between a single binding site of a molecule (e.g., an antibody) and its binding partner (e.g., an antigen).

The term "Omalizumab", as used herein, is recombinant DNA-derived humanized IgG1k monoclonal antibody that specifically binds to free human immunoglobulin E (IgE) in the blood and interstitial fluid and to membrane-bound form of IgE (mIgE) on the surface of mIgE-expressing B lymphocytes. It is an anti-IgE antibody. It is sold under the trade name Xolair®. It binds and neutralizes free IgE and thus reduces the availability of IgE for binding to cellular receptors. Non/reduced availability of IgE to FcεRI cell membrane receptors results in in fewer episodes of airway inflammation, asthma symptoms and exacerbations in patients with severe allergic asthma.

The term "Allergies", as used herein, is a condition caused by hypersensitivity of the immune system to typically harmless substances in the environment. These diseases include hay fever, food allergies, atopic dermatitis, allergic asthma, and anaphylaxis.

The term "allergic asthma", as used herein, is a common long-term inflammatory disease of the airways of the lungs. It is characterized by variable and recurring symptoms, reversible airflow obstruction, and easily triggered bronchospasms. Symptoms include episodes of wheezing, coughing, chest tightness, and shortness of breath. These may occur a few times a day or a few times per week. Depending on the person, asthma symptoms may become worse at night or with exercise.

The term "bioassay", as used herein, is an analytical method to determine concentration or potency of a substance by its effect on living cells or tissues. Bioassays are quantitative biological assays used to estimate the potency of agents by observing their effects on living animals (in vivo) or tissue/cell culture systems (in vitro). A bioassay experiment can be either qualitative or quantitative, direct or indirect.

The term IgE and NP IgE refers to sensitising agent for hFCεRIa receptor.

The term "Bioactivity" refers to neutralization capacity of anti-IgE antibody which leads to the efficacy/potency of the anti-IgE antibody.

The term "first assay mixture" as used herein, is mixture of suitable amount of seeded cells (cell suspension containing cells and Media), suitable amount of antibody of interest, suitable amount of anti NP-IgE in assay plate.

The term "second assay mixture" as used herein, is mixture of first assay mixture with suitable amount of assay buffer to perform washing step.

The term "third assay mixture" as used herein, is mixture of second assay mixture with suitable amount of reagent such as NP-BSA (bovine serum albumin).

The term "fourth assay mixture" as used herein, is mixture of third assay mixture with suitable amount of substrate such as M-NAG.

The term "Suitable physiological temperature" refers to temperature suitable for the cellular function and secretion of selected cell. For instance, if mammalian cells are seeded in plate than suitable temperature is selected from about 25° C. to about 45° C. In an embodiment, the temperature is selected from about 35° C. to about 37° C. In an preferred embodiment, the temperature is about 37° C. In certain embodiment the term room temperature or RT refers to temperature selected from 23° C., 24° C., 25° C., 26° C., 27° C., 28° C., 29° C., 30° C., 31° C., 32° C., 33° C., 34° C., 35° C., 36° C. preferably 37° C.

The term "pre-seeded assay plate" refers to assay plate prepared by seeding the cell and incubating them for 3 hours to 5 hours. Pre-seeded assay plate is used for incorporating sensitized and neutralised IgE or NP-IgE and anti-IgE antibody.

The term "sensitizing and neutralizing" refers to sensitize and neutralize the cell in assay plate wherein the cell express or comprises hFCεRIa receptor. In an embodiment, the cell is RBL 2H3 cell. The present invention performs sensitising and neutralizing activity simultaneously by incorporating the mixture of IgE or NP-IgE and anti-IgE antibody and incubate the assay plate for at least about 18 hours to about 24 hours at room temperature. In preferred embodiment the incubation if performed for 24 hours at room temperature. In an embodiment incubation temperature has more than one temperature wherein the first temperature is lower than second and subsequent temperature. In an embodiment, the first temperature is about 25° C., 26° C., 27° C., 28° C., 29° C. and 30° C. In an embodiment, the second temperature is about 33° C., 34° C., 35° C., 36° C. preferably 37° C. In an embodiment, the first temperature is maintained at least for 1 to 2 hours. In an embodiment, the second temperature is maintained at least for 18 to 24 hours.

The term "Suitable assay buffer" refers to buffer made of suitable excipients selected from calcium, magnesium, potassium, glucose, sodium chloride, sodium buffer and mixture thereof. The assay buffer is required to remove the media from the seeded cell plate. The term "Tyrode's buffer", as used herein, is a solution that is isotonic with interstitial fluid and used in physiological experiments and tissue culture. It contains magnesium, a sugar (usually glucose) as an energy source and uses bicarbonate and phosphate as a buffer. Some variations also include phosphate and sulphate ions. It must be gassed with 95% oxygen and N2, 5% carbon dioxide when used for cell culture applications and physiology experiments in order to achieve an appropriate pH. With the addition of extra potassium salt, it can be used to prepare a cardioplegic solution.

The term "Allergan" refers to IgE or Immunoglobulin E, NP or NP-BSA selected to stimulate the cell to secrete allergic response.

The term "Suitable substrate" refers to compound capable to measure the allergic response by reacting with cell secreted proteins.

The term "degranulation" as used herein, is a cellular process that releases antimicrobial cytotoxic or other molecules from secretory vesicles called granules found inside cells.

The term "comprises" or "comprising" is used in the present description, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

As used throughout the specification and in the appended claims, the singular forms "a," "an," and "the" include the plural reference unless the context clearly dictates otherwise.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

In one of the embodiments, the present invention provides methods and reagents that are useful in measuring the bioactivity anti IgE monoclonal antibody. More specifically, the invention provides bioactivity measurement of Omalizumab compared to reference standard.

In an embodiment, the present invention provides an improved assay method comprising:
a) sensitising of RBL 2H3 cell comprising hFCεRIa receptor with IgE or anti NP IgE and neutralizing the suitable concentration of anti-IgE antibody by incubating at suitable temperature for suitable time;
b) transferring the suitable concentration of sensitized and neutralized mixture of anti-IgE antibody and anti NP-IgE to pre-seeded assay plate;
c) incubating the pre-seeded plate for suitable time at suitable temperature;
d) washing the pre-seeded assay plate;
e) mixing the suitable antigen into pre-seeded assay plate and incubating for at least 2 hours, preferably 70 minutes;
f) transferring the supernatant from the pre-seeded assay plate into test assay plate;
g) incorporating the suitable substrate into test assay plate and incubate for suitable time;
h) determining the bioactivity of anti-IgE antibody.

In an embodiment, the incubation is performed in step (a) for at least about 18 hours to about 24 hours at room temperature.

In an embodiment, the suitable concentration of anti-IgE antibody is varying.

In an embodiment, the varying concentration of anti-IgE antibody is derived from assay plate prepared with varying concentration from higher to lower concentration of anti-IgE antibody with dilution in suitable media.

In an embodiment, the concentration of anti NP-IgE is constant and selected from about 30 μl, about 40 μl, about 50 μl, and about 60 μl.

In an embodiment, the anti-IgE antibody volume is constant in step (b) selected from about 30 μl, about 40 μl, about 50 μl, and about 60 μl.

In an embodiment, the incubation is performed in step (c) from 18 hours, 19 hours, 20 hours, 21 hours, 22 hours, 23 hours, and 24 hours.

In an embodiment, the suitable temperature in step (c) and/or step (e) is about 37° C.

In an embodiment, the washing is performed in step (d) one or more time preferably two times with suitable buffer selected form Tyrode's buffer containing 1% BSA, phosphate buffer, carbonate citrate.

In an embodiment, the suitable antigen is selected from NP-BSA (bovine serum albumin) and anti-IgE antibody.

In an embodiment, the suitable substrate is M-NAG.

In an embodiment, the M-NAG concentration is selected from about 0.5 mM, about 1 mM, about 1.5 mM and about 2 mM.

In an embodiment, the substrate is incubated for 40 minutes, preferable 30 minutes at 37° C.

In an embodiment, the quenching of the assay reaction post step (g) by using ice cold sodium bicarbonate buffer.

In an embodiment, the bioactivity of anti-IgE antibody is determined within 2 days, preferably 1.5 days.

In an embodiment, the bioactivity is determined by using enzyme selected from prostaglandins, leukotrienes, kinins, ECF-A, PAF (platelet activating factor), histamine and B-hexosaminidase preferably ß-hexosaminidase.

In an embodiment, the bioactivity of anti-IgE antibody is determined by B-hexosaminidase degranulation takes less time than histamine release degranulation.

In another embodiment, the present invention further provides mechanism of action based functional bioassay measuring the bioactivity anti IgE monoclonal antibody.

In an embodiment, the present invention provides an improved assay method to determine the bioactivity or efficacy of an antibody comprising:
a) seeding cells in the assay plate with suitable media to form cell suspension;
b) incubating the cell suspension with $CO_2$ at suitable physiological temperature for suitable time;
c) sensitising and neutralizing the antibody of interest and anti NP-IgE simultaneously and incubating the antibody of interest and anti NP-IgE mixture less than 24 hours;
d) transferring the antibody of interest and anti NP-IgE mixture to the seeded assay plate to form assay mixture;
e) incubating the assay mixture at suitable physiological temperature for suitable time;
f) washing the assay mixture with suitable assay buffer;
g) incubating the assay mixture with antigen at suitable physiological temperature for not more than 2 hours;
h) treating the supernatant with suitable substrate in assay plate;
i) measuring the efficacy of the antibody of interest.

In an embodiment, the present invention provides an improved assay method to determine the efficacy of an antibody comprising:
a) seeding RBL-2H3 hFcεR1A cells in the assay plate with MEM media to form cell suspension;
b) incubating the cell suspension with $CO_2$ at suitable physiological temperature for suitable time;
c) sensitising and neutralizing the immunoglobulin E (IgE) antibody and anti NP-IgE simultaneously and incubating the immunoglobulin E (IgE) antibody and anti NP-IgE mixture less than 24 hours;
d) transferring the immunoglobulin E (IgE) antibody and anti NP-IgE mixture to the seeded assay plate to form assay mixture;
e) incubating the assay mixture at suitable physiological temperature for suitable time;
f) washing the assay mixture with Tyrode's buffer containing 1% BSA;
g) incubating the assay mixture with NP-BSA at suitable physiological temperature for not more than 2 hours;
h) reating the supernatant with M-NAG in assay plate;
i) measuring the efficacy of the antibody of interest.

In an embodiment, the present invention provides an improved assay method to determine the efficacy of an antibody comprising:
a) seeding RBL-2H3 hFcεR1A in the assay plate with MEM media to form cell suspension;
b) incubating the cell suspension with $CO_2$ at suitable physiological temperature for suitable time;
c) mixing the immunoglobulin E (IgE) antibody and anti NP-IgE in seeded cell plate;
d) incubating the immunoglobulin E (IgE) antibody and anti NP-IgE mixture in seeded cell plate for less than 24 hours at suitable physiological temperature to form antibody NP-IgE complex;

e) washing the first assay mixture with Tyrode's buffer containing 1% BSA buffer to form second assay mixture;
f) incubating the second assay mixture with suitable amount of NP-BSA (bovine serum albumin) for not more than 2 hours with $CO_2$ at suitable physiological temperature to form third assay mixture;
g) treating the third assay mixture or supernatant derived from it with M-NAG in assay plate to form fourth assay mixture;
h) incubating the fourth assay mixture with $CO_2$ at suitable physiological temperature for suitable time;
i) reading the plate to measure the efficacy of the antibody of interest;
wherein the antibody of interest and anti NP-IgE is incubated for at least 1-2 hours to form neutralised complex of antibody of interest and anti NP-IgE before performing mixing in step (c); wherein the assay provides the less variation in histamine and B-hex.

In an embodiment, the invention represents an improved assay method to determine the efficacy of an antibody the assay method comprising:
a) mixing the allergen-antibody and antibody of interest in the assay plate seeded with suitable cell;
b) incubating the assay plate with $CO_2$ at suitable temperature for suitable time;
c) washing the assay plate with suitable assay buffer;
d) stimulating the suitable cell with suitable stimulator;
e) optionally incubate the assay plate for suitable time;
f) adding the suitable substrate in the assay plate;
g) optionally incubate the assay plate for suitable time;
h) reading the plate to determine efficacy of the antibody of interest.

In an embodiment, the invention represents an improved assay method to determine the efficacy of an antibody the assay method comprising:
a) mixing the allergen-antibody and antibody of interest in the assay plate seeded with suitable cell;
b) incubating the assay plate with $CO_2$ at suitable temperature for suitable time;
c) washing the assay plate with suitable assay buffer;
d) stimulating the suitable cell with suitable stimulator;
e) optionally incubate the assay plate for suitable time;
f) extracting the supernatant from the assay plate;
g) reacting the extracted supernatant with suitable substrate in the assay plate;
h) optionally incubate the assay plate for suitable time;
i) reading the plate to determine efficacy of the antibody of interest.

In an embodiment, the invention represents an improved assay method to determine the efficacy of an antibody the assay method comprising:
a) seeding cells in the assay plate with suitable media to form cell suspension;
b) incubating the cell suspension with $CO_2$ at suitable physiological temperature for suitable time;
c) mixing the antibody of interest and anti NP-IgE in seeded cell plate;
d) incubating the antibody of interest and anti NP-IgE mixture at suitable physiological temperature for suitable time to form antibody NP-IgE complex;
e) perform washing the first assay mixture with suitable assay buffer to form second assay mixture;
f) incubating the second assay mixture with suitable amount of NP-BSA (bovine serum albumin) with $CO_2$ at suitable physiological temperature for suitable time to form third assay mixture;
g) treating the third assay mixture or supernatant derived from it with suitable substrate in assay plate;
h) incubating the fourth assay mixture with $CO_2$ at suitable physiological temperature for suitable time;
i) reading the plate to measure the efficacy of the antibody of interest.

In an embodiment, the invention represents an improved assay method to determine the efficacy of an antibody the assay method comprising:
a) seeding cells in the assay plate with suitable media to form cell suspension;
b) incubating the cell suspension at suitable physiological temperature for suitable time;
c) mixing the antibody of interest and anti NP-IgE in seeded cell plate;
d) incubating the antibody of interest and anti NP-IgE mixture at suitable physiological temperature for suitable time to form antibody NP-IgE complex;
e) mixing the antibody NP-IgE complex into seeded assay plate to form first assay mixture;
f) incubating the first assay mixture at suitable physiological temperature for suitable time;
g) perform washing the first assay mixture with suitable assay buffer to form second assay mixture;
h) incubating the second assay mixture with suitable amount of NP-BSA (bovine serum albumin) at suitable physiological temperature for suitable time to form third assay mixture;
i) treating the third assay mixture or supernatant derived from it with suitable substrate in assay plate;
j) incubating the fourth assay mixture at suitable physiological temperature for suitable time;
k) reading the plate to measure the efficacy of the antibody of interest.

In an embodiment, the invention represents an improved assay method to determine the efficacy of an antibody the assay method comprising:
a) seeding cells in the assay plate with suitable media to form cell suspension;
b) incubating the cell suspension with $CO_2$ at about 35° C. to about 37° C. for suitable time;
c) mixing the antibody of interest and anti NP-IgE in seeded cell plate;
d) incubating the antibody of interest and anti NP-IgE mixture at about 35° C. to about 37° C. for suitable time to form antibody NP-IgE complex;
e) mixing the antibody NP-IgE complex into seeded assay plate to form first assay mixture;
f) incubating the first assay mixture with $CO_2$ at about 35° C. to about 37° C. for suitable time;
g) perform washing the first assay mixture with suitable assay buffer to form second assay mixture;
h) incubating the second assay mixture with suitable amount of NP-BSA (bovine serum albumin) with $CO_2$ at about 25° C. to about 45° C. for suitable time to form third assay mixture;
i) treating the third assay mixture or supernatant derived from it with suitable substrate in assay plate;
j) incubating the fourth assay mixture with CO2 at about 25° C. to about 45° C. for suitable time;
k) reading the plate to measure the efficacy of the antibody of interest.

In an embodiment, the invention represents an improved assay method to determine the efficacy of an antibody the assay method comprising:
a) seeding RBL-2H3 hFcεR1A cells in the assay plate with MEM media to form cell suspension;

b) incubating the cell suspension with 5% $CO_2$ at 37° C. for 4 hours to 5 hours;
c) mixing the antibody of interest and anti NP-IgE in seeded assay plate;
d) incubating the antibody of interest and anti NP-IgE mixture at 37° C. for 1.5 hour to 2 hours to form antibody NP-IgE complex;
e) mixing the antibody NP-IgE complex into seeded assay plate to form first assay mixture;
f) incubating the first assay mixture with 5% $CO_2$ at 37° C. for 18 hours to 24 hours;
g) perform washing twice of first assay mixture with suitable amount Tyrode's buffer containing 1% BSA to form second assay mixture;
h) incubating the second assay mixture with suitable amount of NP-BSA (bovine serum albumin) with 5% $CO_2$ at 37° C. for 60 minutes to form third assay mixture;
i) treating the third assay mixture or supernatant derived from it with M-NAG substrate in assay plate;
j) incubating the fourth assay mixture with $CO_2$ at 37° C. for 30 minutes to 40 minutes;
k) reading the plate to measure the efficacy of the antibody of interest.

In an embodiment, the invention represents an improved assay method to determine the efficacy of an antibody the assay method comprising:
a) seeding RBL-2H3 hFcɛR1A cells in the assay plate with MEM media to form cell suspension;
b) incubating the RBL-2H3 hFcɛR1A cells containing MEM media with about 5% $CO_2$ at about 35° C. to about 37° C. for about 2 hours to about 6 hours;
c) mixing the antibody of interest and anti NP-IgE in seeded cell plate;
d) incubating the antibody of interest and anti NP-IgE mixture at about 35° C. to about 37° C. for about 1 hour to about 2.5 hours to form antibody NP-IgE complex;
e) mixing the antibody NP-IgE complex into seeded assay plate to form first assay mixture;
f) incubating the first assay mixture with about 5% $CO_2$ at about 35° C. to about 37° C. for about 18 hours to about 24 hours;
g) perform washing the first assay mixture with suitable Tyrode's buffer containing 1% BSA to form second assay mixture;
h) incubating the second assay mixture with suitable amount of NP-BSA (bovine serum albumin) with about 5% $CO_2$ at about 25° C. to about 45° C. for about 30 minutes to about 90 minutes to form third assay mixture;
i) treating the third assay mixture or supernatant derived from it with M-NAG substrate in assay plate;
j) incubating the fourth assay mixture with about 5% $CO_2$ at about 25° C. to about 45° C. for about 20 minutes to about 50 minutes;
k) reading the plate to measure the efficacy of the antibody of interest.

In an embodiment, the invention represents an improved assay method to determine the efficacy of an antibody the assay method comprising:
a) seeding RBL-2H3 hFcɛR1A cells in the assay plate with MEM media to form cell suspension;
b) incubating RBL-2H3 hFcɛR1A cells containing MEM media with about 5% $CO_2$ at about 37° C. for about 4 hours to about 5 hours;
c) mixing the about 50 µl of antibody of interest and about 50 µl of anti NP-IgE in seeded cell plate;
d) incubating the antibody of interest and anti NP-IgE mixture at about 37° C. for about 1.5 hour to about 2 hours to form antibody NP-IgE complex;
e) mixing the antibody NP-IgE complex into seeded assay plate to form first assay mixture;
f) incubating the first assay mixture with about 5% $CO_2$ at about 37° C. for about 18° C. hours to about 24 hours;
g) perform washing the first assay mixture with suitable Tyrode's buffer containing 1% BSA to form second assay mixture;
h) incubating the second assay mixture with about 150 µl of about 20 ng/ml NP-BSA (bovine serum albumin) with about 5% $CO_2$ at about 37° C. for about 60° C. minutes to form third assay mixture;
i) treating the third assay mixture or supernatant derived from it with about 50 µl of about 1 mM M-NAG substrate in assay plate;
j) incubating the fourth assay mixture with about 5% $CO_2$ at about 37° C. for about 30 minutes to about 40 minutes;
k) reading the plate to measure the efficacy of the antibody of interest at 360 nm and Em 440 nm.

In another embodiment, the incubation is performed in step (a) for at least about 18 hours to about 24 hours at room temperature.

In another embodiment, the suitable concentration of anti-IgE antibody is varying.

In another embodiment, the varying concentration of anti IgE antibody is derived from assay plate prepared with varying concentration from higher to lower concentration of anti-IgE antibody with dilution in suitable media.

In another embodiment, the concentration of anti NP-IgE is constant and selected from about 30 µl, about 40 µl, about 50 µl, and about 60 µl.

In another embodiment, the anti-IgE antibody volume is constant in step (b) selected from about 30 µl, about 40 µl, about 50 µl, and about 60 µl.

In another embodiment, the incubation is performed in step (c) from 18 hours, 19 hours, 20 hours, 21 hours, 22 hours, 23 hours and 24 hours.

In another embodiment, the suitable temperature in step (c) and/or step (e) is about 37° C.

In another embodiment, the washing is performed in step (d) one or more time preferably two times with suitable buffer selected form Tyrode's buffer containing 1% BSA, phosphate buffer, carbonate citrate.

In another embodiment, the suitable antigen is selected from NP-BSA (bovine serum albumin) and anti-IgE antibody.

In another embodiment, the suitable substrate is M-NAG.

In another embodiment, the M-NAG concentration is selected from about 0.5 mM, about 1 mM, about 1.5 mM and about 2 mM.

In another embodiment, the bioactivity of anti-IgE antibody is determined within 2 days.

In another embodiment, the bioactivity is determined by using enzyme selected from prostaglandins, leukotrienes, kinins, ECF-A, PAF (platelet activating factor), histamine and ß-hexosaminidase preferably ß-hexosaminidase.

In another embodiment, the bioactivity of anti-IgE antibody is determined by B-hexosaminidase degranulation takes less time than histamine degranulation.

In an embodiment, cell is selected from RBL-2H3 hFcɛR1A cell line.

In another embodiment, seeding RBL-2H3 hFcεR1A cells on the seeded plate with MEM media (Minimum Essential media) to form cell suspension.

In another embodiment, the present invention provides media compositions are selected from MEM, RPMI1620, DMEM, FBS. In another embodiment, most preferred media is MEM media.

In an embodiment, of the present invention media compositions are present with concentration of 10% to 20%.

In another embodiment, seeding 96 well cell culture plate with 100 µl/well of cell suspension containing RBL-2H3 hFcεR1A cells and MEM media.

In another embodiment, the density of cell suspension is about $0.3 \times 10^6$ cells/ml.

In an embodiment, after seeding incubate the cell RBL-2H3 hFcεR1A for suitable time. In another embodiment, after seeding incubate the cell RBL-2H3 hFcεR1A for the suitable time is about 2 hours, about 3 hours, about 4 hours, about 5 hours and about 6 hours. In another embodiment, the after seeding incubate the cell RBL-2H3 hFcεR1A for the preferred time is about 4 hours to about 5 hours.

In an embodiment, after seeding incubate the cell RBL-2H3 hFcεR1A for suitable time with suitable physiological temperature. In another embodiment, after seeding incubate the cell RBL-2H3 hFcεR1A for the suitable physiological temperature is about 35° C., about 36° C. and about 37° C. In another embodiment, after seeding incubate the cell RBL-2H3 hFcεR1A the preferred time is about 37° C.

In an embodiment, incubate the cell RBL-2H3 hFcεR1A in presence of $CO_2$. In another embodiment, incubate the cell RBL-2H3 hFcεR1A in presence of about 5% $CO_2$.

In another embodiment, mixing the antibody of interest with anti NP-IgE in assay plate.

In another embodiment, the antibody of interest and anti NP-IgE is added in the seeded cell plate simultaneously.

In another embodiment, the antibody of interest with anti NP-IgE is incubated in the assay plate to form antibody NP-IgE complex before mixing into seeded cell plate.

In another embodiment, incubate the cell suspension containing the mixture of antibody of interest with IgE with suitable amount of NP-BSA (bovine serum albumin) at suitable temperature is about 25° C. to about 45° C. In another embodiment, incubate the cell suspension containing the mixture of antibody of interest with IgE with suitable amount of NP-BSA (bovine serum albumin) for preferred temperature is about 35° C. to about 37° C. In another embodiment, incubate the cell suspension containing the mixture of antibody of interest with IgE with suitable amount of NP-BSA (bovine serum albumin) for most preferred temperature is about 37° C.

In an embodiment, incubate the cell suspension containing the mixture of antibody of interest with IgE with suitable amount of NP-BSA (bovine serum albumin) in presence of 5% $CO_2$ at 37° C. for about 60 minutes.

In another embodiment, the antibody of interest is Humanized monoclonal antibody.

In another embodiment, the antibody of interest is immunoglobulin E (IgE) antibody.

In another embodiment, the antibody of interest is Omalizumab.

In an embodiment, the dose of antibody of interest is selected from about 30 µl, about 40 µl, about 50 µl, and about 60 µl. In another embodiment, the preferred dose of antibody of interest is about 50 µl.

In an embodiment, the volume of anti NP-IgE is selected from about 30 µl, about 40 µl, about 50 µl, and about 60 µl. In another embodiment, the preferred volume of anti NP-IgE is about 50 µl.

In another embodiment, the volume of IgE is selected from about 30 µl, about 40 µl, about 50 µl, and about 60 µl. In another embodiment, the preferred volume of IgE is about 50 µl.

In an embodiment, incubating the mixture of antibody of interest with anti NP-IgE or IgE for suitable time. In another embodiment, incubating the mixture of antibody of interest with anti NP-IgE or IgE for the suitable time is about 1 hour, about 1.5 hours, and about 2 hours. In another embodiment, incubating the mixture of antibody of interest with anti NP-IgE or IgE for the preferred time is about 1.5 hours to about 2 hours.

In an embodiment, incubating the mixture of antibody of interest with anti NP-IgE or IgE with suitable physiological temperature. In preferred embodiment, incubating the mixture of antibody of interest with anti NP-IgE or IgE at room temperature.

In an embodiment, transferring the incubated mixture of antibody of interest with anti NP-IgE or IgE to the assay plate containing the cell suspension to form first assay mixture.

In an embodiment, transferring the incubated mixture of antibody of interest with anti NP-IgE to the assay plate containing the cell suspension (cells and media). In another embodiment, transferring the incubated mixture of antibody of interest with anti NP-IgE of the volume selected from about 30 µl, about 40 µl, about 50 µl, and about 60 µl to the assay plate containing the cell suspension (cells and media). In another embodiment, transferring the incubated mixture of antibody of interest with anti NP-IgE of the preferred volume is about 50 µl to the assay plate containing the cell suspension (cells and media).

In another embodiment, cell suspension does not require washing before mixing with mixture of antibody of interest with anti NP-IgE.

In an embodiment, incubate the cell suspension containing the mixture of antibody of interest with anti NP-IgE for suitable time. In another embodiment, incubate the cell suspension containing the mixture of antibody of interest with anti NP-IgE for suitable time is about 15 hours to 24 hours. In another embodiment, incubate the cell suspension containing the mixture of antibody of interest with anti NP-IgE for suitable time is selected from about 15 hours, about 16 hours, about 17 hours, about 18 hours, about 19 hours, about 20 hours, about 21 hours, about 22 hours, about 23 hours, about 24 hours. In another embodiment, incubate the cell suspension containing the mixture of antibody of interest with anti NP-IgE for preferred time is about 18 hours to about 24 hours.

In an embodiment, incubate the cell suspension containing the mixture of antibody of interest with anti NP-IgE in presence of $CO_2$. In another embodiment, incubate the cell suspension containing the mixture of antibody of interest with anti NP-IgE in presence of about 5% $CO_2$.

In an embodiment, incubate the cell suspension containing the mixture of antibody of interest with anti NP-IgE for suitable physiological temperature. In another embodiment, incubate the cell suspension containing the mixture of antibody of interest with anti NP-IgE for suitable physiological temperature is selected from about 35° C., about 36° C. and about 37° C. In another embodiment, incubate the cell suspension containing the mixture of antibody of interest with anti NP-IgE for preferred temperature is about 37° C.

In another embodiment, incubate the cell suspension containing the mixture of antibody of interest with anti NP-IgE for about 18 hours to about 24 hours in presence of about 5% $CO_2$ at 37° C.

In another embodiment, incubate the cell suspension containing the mixture of antibody of interest with anti NP-IgE for overnight in presence of about 5% $CO_2$ at 37° C.

In an embodiment, the washing the cell suspension containing the mixture of antibody of interest with anti NP-IgE with suitable assay buffer (Tyrode's buffer containing 1% BSA) to form second assay mixture.

In an embodiment, the washing the cell suspension containing the mixture of antibody of interest with anti NP-IgE for one time, two times, three times with suitable assay buffer. In another embodiment, washing the cell suspension containing the mixture of antibody of interest with anti NP-IgE for two times with suitable assay buffer.

In an embodiment, the assay buffer is selected from Tyrode's buffer, phosphate buffer, carbonate citrate. In an embodiment, the assay buffer is selected from Tyrode's buffer containing 1% BSA (Bovine Serum Albumin).

In an embodiment, the volume of assay buffer is selected from about 150 µl, about 160 µl, about 170 µl, about 180 µl, about 190 µl, about 200 µl, about 210 µl, about 220 µl, about 230 µl, about 240 µl, about 250 µl. In another embodiment, the preferred volume of assay buffer is about 200 µl.

In an embodiment, the concentration of assay buffer is selected from about 5 ng/ml, about 10 ng/ml, about 15 ng/ml, about 20 ng/ml, about 25 ng/ml and about 30 ng/ml. In another embodiment, the preferred concentration of assay buffer is about 20 ng/ml.

In an embodiment, incubate the cell suspension containing the mixture of antibody of interest with anti NP-IgE with suitable amount of NP-BSA (bovine serum albumin) to form third assay mixture.

In an embodiment, incubate the cell suspension containing the mixture of antibody of interest with anti NP-IgE with suitable amount of NP-BSA (bovine serum albumin) for suitable time. In another embodiment, incubate the cell suspension containing the mixture of antibody of interest with anti NP-IgE with suitable amount of NP-BSA (bovine serum albumin) for suitable time is about 10 minutes to about 150 minutes. In another embodiment, incubate the cell suspension containing the mixture of antibody of interest with anti NP-IgE with suitable amount of NP-BSA (bovine serum albumin) for suitable time is about 10 minutes, about 20 minutes, about 30 minutes, about 40 minutes, about 50 minutes, about 60 minutes, about 70 minutes, about 80 minutes, about 90 minutes, about 100 minutes, about 120 minutes, about 130 minutes, about 140 minutes and about 150 minutes. In another embodiment, incubate the cell suspension containing the mixture of antibody of interest with anti NP-IgE with suitable amount of NP-BSA (bovine serum albumin) for preferred time is about 30 minutes to about 60 minutes. In another embodiment, incubate the cell suspension containing the mixture of antibody of interest with anti NP-IgE with suitable amount of NP-BSA (bovine serum albumin) for most preferred time is about 60 minutes.

In an embodiment, incubate the cell suspension containing the mixture of antibody of interest with anti NP-IgE with suitable amount of NP-BSA (bovine serum albumin) in presence of $CO_2$. In another embodiment, incubate the cell suspension containing the mixture of antibody of interest with anti NP-IgE with suitable amount of NP-BSA (bovine serum albumin) in presence of about 5% $CO_2$.

In an embodiment, incubate the cell suspension containing the mixture of antibody of interest with anti NP-IgE with suitable amount of NP-BSA (bovine serum albumin) for suitable temperature. In another embodiment, incubate the cell suspension containing the mixture of antibody of interest with anti NP-IgE with suitable amount of NP-BSA (bovine serum albumin) for suitable temperature is about 25° C. to about 45° C. In another embodiment, incubate the cell suspension containing the mixture of antibody of interest with anti NP-IgE with suitable amount of NP-BSA (bovine serum albumin) for preferred temperature is about 35° C. to about 37° C. In another embodiment, incubate the cell suspension containing the mixture of antibody of interest with anti NP-IgE with suitable amount of NP-BSA (bovine serum albumin) for most preferred temperature is about 37° C.

In an embodiment, incubate the cell suspension containing the mixture of antibody of interest with anti NP-IgE with suitable amount of NP-BSA (bovine serum albumin) in presence of 5% $CO_2$ at 37° C. for about 60 minutes.

In an embodiment, harvest the supernatant form the incubated mixture of antibody anti NP-IgE complex and NP-BSA.

In an embodiment, mixing the mixture of cell suspension containing the mixture of antibody of interest with anti NP-IgE with suitable amount of NP-BSA after incubation which provides cell supernatant with suitable substrate.

In an embodiment, the mixture of antibody anti NP-IgE complex and NP-BSA with substrate M-NAG to form fourth assay mixture.

In an embodiment, the preferred substrate is M-NAG (4-methylumbelliferyl-N-acetyl-β-D-glucosamine).

In an embodiment, the concentration of M-NAG is selected from about 0.5 mM, about 1 mM, about 1.5 mM, about 2 mM. In an embodiment, the preferred concentration of M-NAG is about 1 mM.

In an embodiment, the volume of M-NAG is selected from about 30 µl, about 40 µl, about 50 µl, and about 60 µl. In an embodiment, the preferred volume of M-NAG is about 50 µl.

In an embodiment, the volume of cell supernatant is selected from about 30 µl, about 40 µl, about 50 µl, and about 60 µl. In an embodiment, the preferred volume of cell supernatant is 50 µl.

In an embodiment, incubating the assay plate containing cell supernatant with M-NAG substrate with suitable time. In another embodiment, incubating the assay plate containing cell supernatant with M-NAG substrate with about 20 minutes to about 50 minutes. In another embodiment, incubating the assay plate containing cell supernatant with M-NAG substrate with about 20 minutes, about 30 minutes, about 40 minutes and about 50 minutes. In another embodiment, incubating the assay plate containing cell supernatant with M-NAG substrate with preferred time is about 30 minutes to about 40 minutes.

In an embodiment, incubating the assay plate containing cell supernatant with M-NAG substrate for suitable physiological temperature. In another embodiment, incubating the assay plate containing cell supernatant with M-NAG substrate for suitable temperature is about 25° C. to about 45° C. In another embodiment, incubating the assay plate containing cell supernatant with M-NAG substrate for suitable temperature is about 35° C. to about 37° C. In another embodiment, incubating the assay plate containing cell supernatant with M-NAG substrate for most preferred temperature is about 37° C.

In an embodiment, incubating the assay plate containing cell supernatant with M-NAG substrate in presence of $CO_2$. In another embodiment, incubating the assay plate containing cell supernatant with M-NAG substrate in presence of about 5% $CO_2$.

In an embodiment, incubate the cell supernatant containing substrate M-NAG in presence of 5% $CO_2$ at 37° C. to about 30 minutes to about 40 minutes.

In an embodiment, after incubation add suitable volume of buffer to incubated cell supernatant.

In an embodiment, the buffer is selected from sodium carbonate buffer.

In an embodiment, the volume of buffer is selected from about 100 μl to about 200 μl. In an embodiment, the preferred volume of buffer is about 100 μl.

In an embodiment, the reading the plate to determine bioactivity or efficacy of antibody of interest by measuring florescence.

In an embodiment, the reading the plate to determine bioactivity or efficacy of antibody of interest by measuring florescence Ex 360 nm and Em 440 nm.

In an embodiment, the said assay method provides better analysis of antibody.

In an embodiment, the said assay method provides results in less than 2 days.

In another embodiment, the present invention provides method and reagents that are useful in measuring the bioactivity anti IgE monoclonal antibody wherein enzymes use in the methods provided herein include, for example, prostaglandins, leukotrienes, kinins, ECF-A, PAF (platelet activating factor), histamine and ß-hexosaminidase. Preferred enzymes used here in bioassay is ß-hexosaminidase.

In an embodiment, the present invention relates to methods or bioassay for detecting the presence of IgE antibodies in a sample, and more particularly to methods for detecting IgE antibodies in the presence of a drug in the sample.

In an embodiment, the present invention provides a method for evaluating the efficacy of an antibody that binds IgE comprising measuring the ability of a biological sample treated with the anti-IgE monoclonal antibody to block a biological activity of the IgE antibody.

In an embodiment, the invention concerns a method of determining degranulation, wherein reduction in the degranulation indicates the presence of neutralizing antibodies in the biological sample.

In an embodiment, the present invention related to B-hexosaminidase degranulation assay is rapid (takes less time), effective and economic than the Histamine release assay.

In an embodiment, the present invention relates to optimization of B-hexosaminidase degranulation actual mechanism in anti-IgE antibody compared with Histamine release functional assay. In an embodiment, the invention provides similar relative potency degranulation with Beta Hex than % potency of histamine assay.

In an embodiment, the Histamine release involved a preincubation of cells for 4-5 hours post seeding which time is higher in known art.

In an embodiment, of the present invention, the degranulation and release of proinflammatory mediators are histamine, tryptase, leukotrienes, In an embodiment of the present invention, degranulation was measured using a fluorescence method.

In an embodiment, the invention provides better relative potency degranulation with Beta Hex than % potency of histamine assay.

In an embodiment, the Histamine release involved a preincubation of cells for less than 5 hours post seeding, preferably 4 to 5 hours.

In embodiment, the bioassay assay procedure is completed in 2 days (48 hours) preferably 1.5 days (35 hours) by performing sensitization and neutralization simultaneously. In certain embodiment, the centrifugation step is further removed. In certain embodiment, the invention further reduces incubation time for the preparation of pre-seeded plate preparation. In an embodiment, the pre-seeded plate is prepared by performing 4 hours incubation.

In an embodiment, the B-hexamindase based degranulation detection step takes less than 3 hours.

The present invention provides an illustrative example but the scope the invention should not be considered limiting to them.

Solution Preparation and Conditions:

Buffer A: Citric Acid Composition and Preparation

Dissolved the 19.2 g citric acid in 800 ml of purified water make up to 1 L.

Buffer B: Tri-Sodium Composition and Preparation

Dissolved the 29.4 g Tri-sodium citrate in 800 ml of purified water make up to 1 L.

Citrate Buffer Composition and Preparation

| Sr. No | Buffer Component | Volume |
|---|---|---|
| 1. | Buffer A: 0.1M Citric acid | 445 ml |
| 2. | Buffer B: 0.1M Tri-sodium citrate | 555 ml |

Sodium Carbonate Buffer Composition and Preparation

Dissolved 1.048 g Sodium bicarbonate and 9.276 g Sodium carbonate anhydrous in 800 ml of purified water and make up to 1 L.

Tyrode's Buffer Composition and Preparation

| Sr. No. | Material | Weight (gram) |
|---|---|---|
| 1. | D-Glucose | 1.00 |
| 2. | Sodium phosphate dibasic | 0.058 |
| 3. | Sodium chloride | 8.00 |
| 4. | Sodium bicarbonate | 1.00 |
| 5. | Potassium chloride | 0.200 |
| 6. | Magnesium chloride | 0.138 |
| 7. | Calcium chloride | 0.200 |

Dissolved and make up to 1 L with water. pH to 7.4±0.2 using 0.1 M HCL or 0.1 M NaOH.

Preparation of Assay Buffer

Assay buffer is prepared by mixing 72.5 ml Tyrode's buffer and 2.5 ml BSA solution (30%) in appropriate tube/bottle.

Complete MEM Media Composition and Preparation

| Sr. No. | Material | Volume | Final concentration (In 585.5 mL) |
|---|---|---|---|
| 1. | MEM | 500 ml | — |
| 2. | FBS | 80 ml | 13.7% |
| 3. | Pen Strep | 5.5 ml | 1X |
| 4. | Puromycin (10 mg/ml) | 29 μl | 0.5 μg |

Added all the contents to the bottle containing MEM and mix.

1 mM MNAG (Substrate) Preparation

| S. No. | Material | Weight/Volume |
|---|---|---|
| 1. | MNAG | 5 mg |
| 2. | Citrate buffer | 13.2 ml |

Reconstitution of NP-BSA

| Sr. No. | Material | Weight/Volume |
|---|---|---|
| 1. | NP BSA | 10 mg |
| 2. | Sterile water | 1 ml |

Reconstituted 10 mg NP-BSA in 1 ml sterile water. After complete dissolution, transferred 950 µl to 8.55 ml sterile water to make 1 mg/ml stock.

1% Triton-X 100 Lysis Buffer Preparation

| S. No. | Material | Weight/Volume |
|---|---|---|
| 1. | Triton-X 100 | 1 ml |
| 2. | Milli-Q water | 99 ml |

Mixed by vertexing or by using magnetic beads.

Example 1

β-Hexosaminidase Degranulation Assay
Cell line: RBL2H3 hFCe RIA clone 7

96 well cell culture plate is seeded with 100 µl/well of cell suspension ($0.3 \times 10^6$ cells/ml) and incubated at 37° C.±0.5° C. and 5%±1% $CO_2$ for 4 hours. 50 µl of different dose of sample is mixed and 50 µl of anti NP-IgE is diluted. This mixture is incubated at RT for 1.5 hours. After incubation, 50 µl of drug-anti NP IgE mixture is transferred to cell containing plate and further this mixture is incubated for overnight (18 hours) in $CO_2$ incubator at 37° C. with 5% $CO_2$. After overnight incubation, cells are washed twice with 200 µl of assay buffer and then incubated with 150 µl of 20 ng/ml NP-BSA for 1 hr±10 minute in $CO_2$ incubator at 37° C. with 5% $CO_2$. After incubation, 50 µl of cell supernatant and 50 µl of 1 mM M-NAG substrate is added in 96 well black plate. The plate is incubated at 37° C. and 5% $CO_2$ for 30 minutes. After incubation, 150 µl of cold sodium carbonate buffer is added. Florescence of plate is measured at Ex 360 nm and Ex 440 nm.

Omalizumab β-Hexosaminidase Degranulation Assay Procedure

Day 1
  Cell seeding in 96 well TC assay Plate (Plate 1 pre-seeded cell plate)
  Serial dilution of Test/Reference sample in deep well plate to vary anti-IgE concentration from higher to lower concentration (Plate 2)
  Incubation of diluted Test/Reference sample (anti-IgE) with anti-NP IgE in V-bottom plate (Plate 3 neutralization plate)
  Sensitization of cells and neutralization of antibody in plate 1 by incorporating mixture of anti-NP-IgE and anti-IgE from plate 3

Day 2
  Washing and Stimulation of cells with NP-BSA (Plate 1)
  Transfer of assay samples from plate 1 to new V-bottom plate (Plate 4)
  Detection of β-hexosaminidase activity in clear bottom black plate (Plate 5)
  Reading and Data analysis Histamine Release Assay
Cell line: RBL2H3 hFCe R1A clone 7

β-hexosaminidase degranulation is performed on Day 1. β-hexosaminidase degranulation is performed on Day 2 and collected supernatant. 50 µl indicator buffer is added in all assay wells. In 2 mL 96 well plate, 50 µl of each sample and/or controls and/or kit standards are added. 10 µl of Acylation reagent is added in all assay wells. The plate is covered and incubated for at least 30 minutes at room temperature. 1.8 mL of 1× assay buffer is added and mixed properly. In the microtiter plate, 50 µl of Acylated samples are added as per plate layout. 50 µl of freshly prepared 1× enzyme conjugate. 50 µl of histamine antiserum is added. Incubated at room temperature for at least 3 hours on at 500 rpm. 250 µl wash buffer is used to wash the plate 4 times. 100 µl of TMB substrate solution is added. 100 µl of TMB stop solution is added to stop the substrate reaction. Absorbance is measured at 450 nm wavelength within 15 minutes after adding stop solution.

Comparison of Relative Potency (%) Degranulation and % Potency of Histamine

| Sample Number | Relative Potency (%) Degranulation | % Potency of Histamine |
|---|---|---|
| 1 | 105 | 99.9 |
| 2 | 102.2 | 98.1 |
| 3 | 105 | 101.9 |
| 4 | 105 | 107.3 |
| 5 | 98.55 | 101.3 |
| 6 | 90.8 | 95.1 |
| 7 | 90.15 | 86 |
| 8 | 94.8 | 93.4 |
| 9 | 101.75 | 102.2 |

Relative potency results from B-hex degranulation assay are comparable with that of histamine release assay. Degranulation assay is performed as a biochemical assay and hence the assay turnaround time is shorter in comparing to histamine release assay, an ELISA based technique. The B-hex degranulation assay takes 30 minutes with M-NAG substrate while Histaminase assay in the present example still takes addition 4 hours 30 min treatment with substrate. Therefore, it is evident that current assay method can be completed in 1.5 days (within 35 hours).

Example 2

β-Hexosaminidase Degranulation Assay
Cell line: RBL2H3 hFCe R1A clone 7

96 well cell culture plate is seeded with 100 µl/well of cell suspension ($0.3 \times 10^6$ cells/ml) and incubated at 37° C.±0.5° C. and 5%±1% $CO_2$ for 5 hours. 50 µl of different dose of sample is mixed and 50 µl of anti NP-IgE is diluted. This mixture is incubated at RT for 2 hours. After incubation, 50 µl of drug-anti NP IgE mixture is transferred to cell containing plate and further this mixture is incubated for overnight (24 hours) in $CO_2$ incubator at 37° C. with 5% $CO_2$. After overnight incubation, cells are washed twice with 200 µl of assay buffer and then incubated with 150 µl of 20 ng/ml NP-BSA for 1 hr±10 minute in $CO_2$ incubator at 37° C. with 5% $CO_2$. After incubation, 50 μl of cell supernatant and 50 μl of 1 mM M-NAG substrate is added in 96 well black plate. The plate is incubated at 37° C. and 5% $CO_2$ for 40 minutes. After incubation, 150 μl of cold sodium carbonate buffer is added. Florescence of plate is measured at Ex 360 nm and Ex 440 nm.

Omalizumab β-Hexosaminidase Degranulation Assay Procedure

Day 1
 Cell seeding in 96 well TC assay Plate (Plate 1 pre-seeded cell plate)
 Serial dilution of Test/Reference sample in deep well plate to vary anti-IgE concentration from higher to lower concentration (Plate 2)
 Incubation of diluted Test/Reference sample (anti-IgE) with anti-NP IgE in V-bottom plate (Plate 3 neutralization plate)
 Sensitization of cells and neutralization of antibody in plate 1 by incorporating mixture of anti-NP-IgE and anti-IgE from plate 3

Day 2
 Washing and Stimulation of cells with NP-BSA (Plate 1)
 Transfer of assay samples from plate 1 to new V-bottom plate (Plate 4)
 Detection of β-hexosaminidase activity in clear bottom black plate (Plate 5)
 Reading and Data analysis Histamine Release Assay
 Cell line: RBL2H3 hFCe R1A clone 7
 β-hexosaminidase degranulation is performed on Day 1. β-hexosaminidase degranulation is performed on Day 2 and collected supernatant. 50 μl indicator buffer is added in all assay wells. In 2 mL 96 well plate, 50 μl of each sample and/or controls and/or kit standards are added. 10 μl of Acylation reagent is added in all assay wells. The plate is covered and incubated for at least 30 minutes at room temperature. 1.8 mL of 1× assay buffer is added and mixed properly. In the microtiter plate, 50 μl of Acylated samples are added as per plate layout. 50 μl of freshly prepared 1× enzyme conjugate. 50 μl of histamine antiserum is added. Incubated at room temperature for at least 3 hours on at 500 rpm. 250 μl wash buffer is used to wash the plate 4 times. 100 μl of TMB substrate solution is added. 100 μl of TMB stop solution is added to stop the substrate reaction. Absorbance is measured at 450 nm wavelength within 15 minutes after adding stop solution.

Comparison of Relative Potency (%) Degranulation and % Potency of Histamine

| Sample Number | Relative Potency (%) Degranulation | % Potency of Histamine |
|---|---|---|
| 1 | 105 | 99.9 |
| 2 | 102.2 | 98.1 |
| 3 | 105 | 101.9 |
| 4 | 105 | 107.3 |
| 5 | 98.55 | 101.3 |
| 6 | 90.8 | 95.1 |
| 7 | 90.15 | 86 |
| 8 | 94.8 | 93.4 |
| 9 | 101.75 | 102.2 |

Relative potency results from B-hex degranulation assay is comparable with that of histamine release assay. Degranulation assay is performed as a biochemical assay and hence the assay turnaround time is shorter in comparing to histamine release assay, an ELISA based technique. The B-hex degranulation assay takes 40 minutes with M-NAG substrate while Histaminase assay in the present example still takes addition 4 hours 30 min treatment with substrate. Therefore, it is evident that current assay method can be completed in 1.5 days (within 35 hours).

Example 3

Relative Accuracy and Precision Evaluation of the β-Hexosaminidase Degranulation Assay and Histamine Release ELISA Cell line: RBL2H3 hFCe R1A clone 7
 96 well cell culture plate is seeded with 100 μl/well of cell suspension (0.3×10⁶ cells/ml) and incubated at 37° C.±0.5° C. and 5%±1% $CO_2$ for 4 hours. 50 μl of different dose of reference standard and Sample at different potency levels i.e 60%, 80%, 100%, 125% and 156% are mixed and 50 μl of anti NP-IgE is diluted. This mixture is incubated at RT for 1.5 hours. After incubation, 50 μl of drug-anti NP IgE mixture is transferred to cell containing plate and further this mixture is incubated for overnight (18 hours) in $CO_2$ incubator at 37° C. with 5% $CO_2$. After overnight incubation, cells are washed twice with 200 μl of assay buffer and then incubated with 150 μl of 20 ng/ml NP-BSA for 1 hr±10 minute in $CO_2$ incubator at 37° C. with 5% $CO_2$. After incubation, 50 μl of cell supernatant and 50 μl of 1 mM M-NAG substrate is added in 96 well black plate. The plate is incubated at 37° C. and 5% $CO_2$ for 30 minutes. After incubation, 150 μl of cold sodium carbonate buffer is added. Florescence of plate is measured at Ex 360 nm and Ex 440 nm.

Relative accuracy and precision is analysed with different potency, six replicates for each level by two analyst for Beta hexosaminidase as per USP chapter 1033

Histamine Release Assay
 Cell line: RBL2H3 hFCe R1A clone 7
 β-hexosaminidase degranulation is performed on Day 1. β-hexosaminidase degranulation is performed on Day 2 and collected supernatant. 50 μl indicator buffer is added in all assay wells. Which has different potency level 50 μl of different dose of reference standard and Sample at different potency levels i.e 60%, 80%, 100%, 125% and 156%. In 2 mL 96 well plate, 50 μl of each sample and/or controls and/or kit standards are added. 10 μl of Acylation reagent is added in all assay wells. The plate is covered and incubated for at least 30 minutes at room temperature. 1.8 mL of 1× assay buffer is added and mixed properly. In the microtiter plate, 50 μl of Acylated samples are added as per plate layout. 50 μl of freshly prepared 1× enzyme conjugate. 50 μl of histamine antiserum is added. Incubated at room temperature for at least 3 hours on at 500 rpm. 250 μl wash buffer is used to wash the plate 4 times. 100 μl of TMB substrate solution is added. 100 μl of TMB stop solution is added to stop the substrate reaction. Absorbance is measured at 450 nm wavelength within 15 minutes after adding stop solution.

Relative accuracy and precision is analysed with different potency, six replicates for each level by two analyst for Histamine Release assay as per USP chapter 1033

Figure 4:
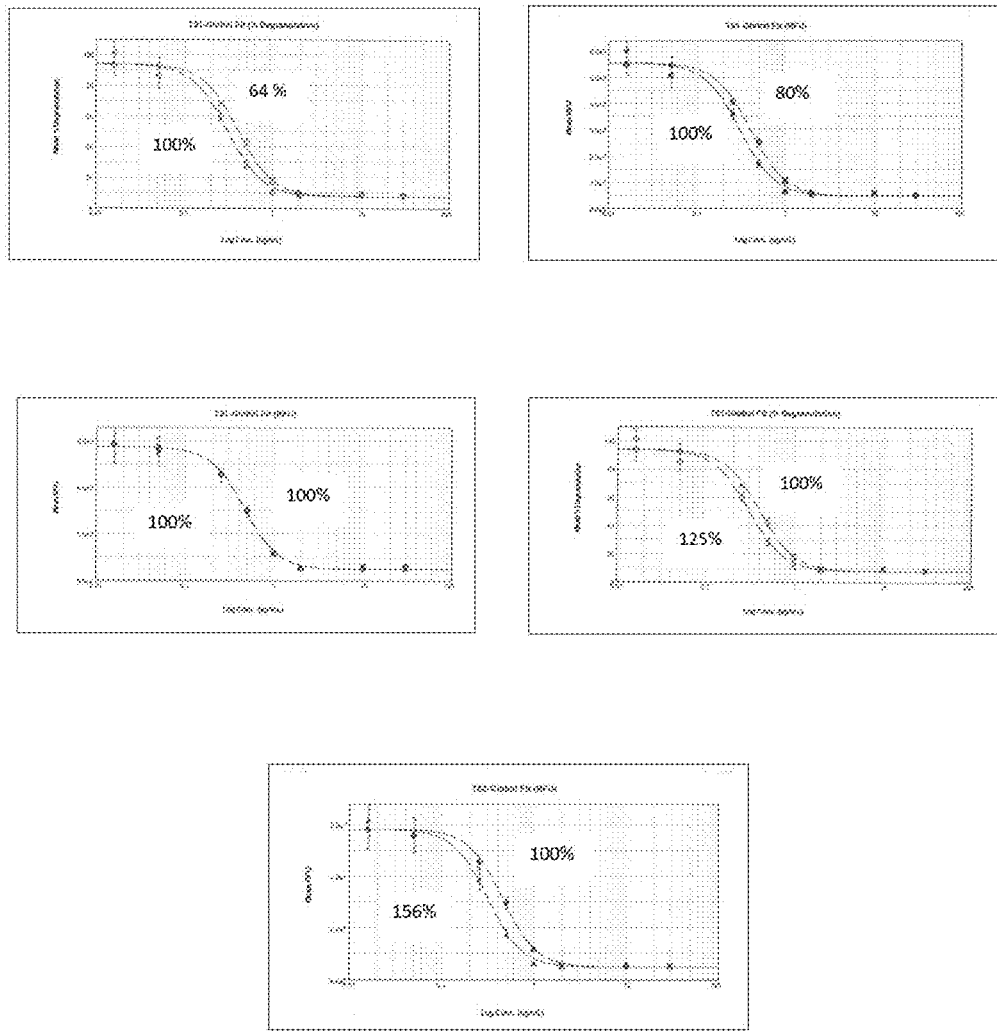
FIG. 4: Representative graph of beta hex degranulation assay
Figure 5:
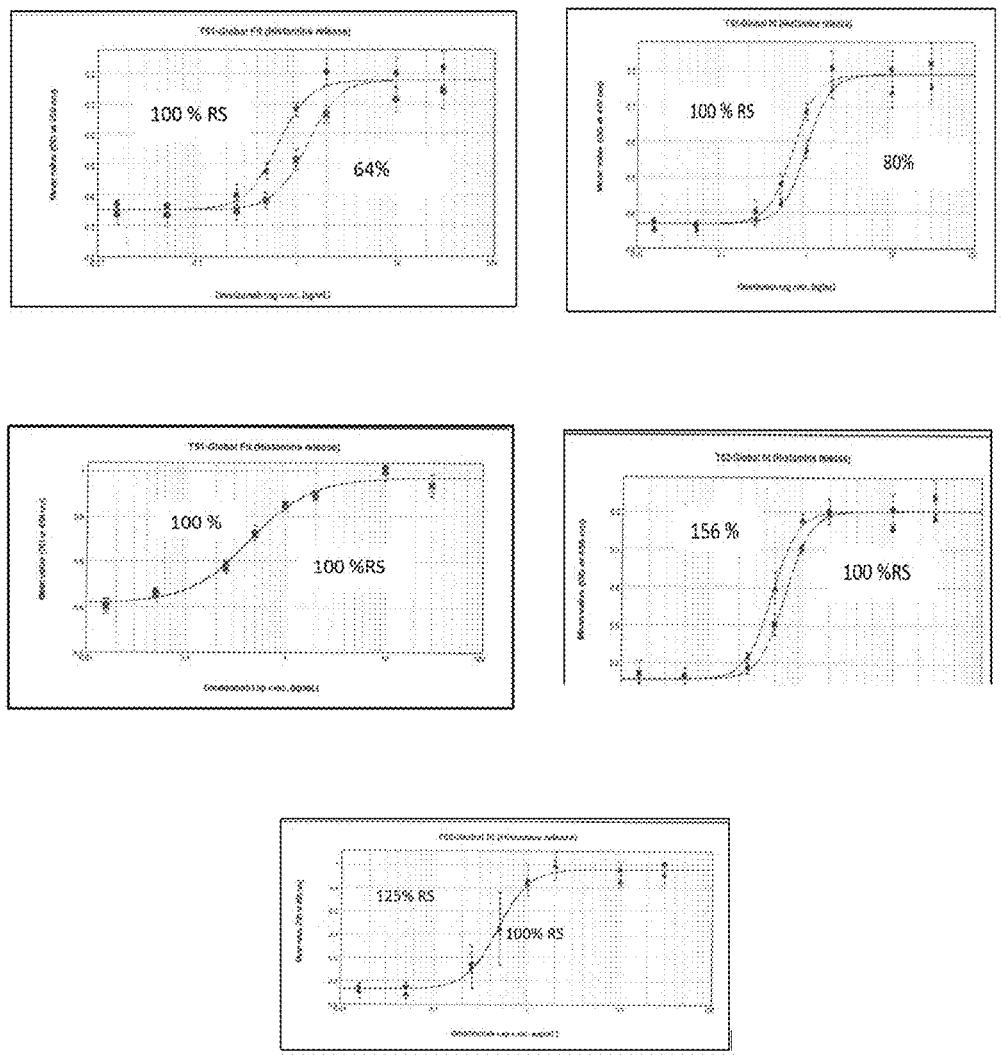
FIG. 5: Representative graph of Histamine Release Assay

| Qualification Parameter | Beta Hex degranulation Assay (representative; FIG. 4) | Histamine Release assay (representative; FIG. 5) |
| --- | --- | --- |
| Precision | Maximum variation Intra plate is 10.40%. Maximum variation Inter plate is 8.18%. Overall % RSD is 8.72%. Maximum variation is 13.66%. | Maximum % RSD for Intra plate is 23.54%. Maximum % RSD for Inter plate is 16.24%. Overall % RSD is 9.79%. Maximum variation is 18.77%, |
| Accuracy | % Recovery at 64% is 103.4%. % Recovery of 80% is 100.8%. % Recovery of 100% is 102.7%. % Recovery of 125% is 103.9%. % Recovery of 156% is 99.5%. Each potency level is within 99.5-103.9%. | % Recovery at 64% is 93.2. % Recovery of 80% is 91.4. % Recovery of 100% is 97.2. % Recovery of 125% is 99.3. % Recovery of 156% is 96.8. Each potency level is within 70-130%. |

High variation in precision results to inconsistency in results for the determination of the potency while % recovery away from 100% leads to results inaccuracy in Potency.

Beta hex-degranulation assay is more precise as the variation is less in comparison to histamine release assay. Further, Beta hex-degranulation assay recovery is around 100% makes it accurate as compared to histamine release assay.

Example 4

Relative Accuracy and Precision Evaluation of the β-Hexosaminidase Degranulation Assay and Histamine Release ELISA Cell line: RBL2H3 hFCe R1A clone 7

96 well cell culture plate is seeded with 100 µl/well of cell suspension (0.3×10⁶ cells/ml) and incubated at 37° C.±0.5° C. and 5%±1% $CO_2$ for 5 hours. 50 µl of different dose of reference standard and Sample at different potency levels i.e 60%, 80%, 100%, 125% and 156% are mixed and 50 µl of anti NP-IgE is diluted. This mixture is incubated at RT for 2 hours. After incubation, 50 µl of drug-anti NP IgE mixture is transferred to cell containing plate and further this mixture is incubated for overnight (24 hours) in $CO_2$ incubator at 37° C. with 5% $CO_2$. After overnight incubation, cells are washed twice with 200 µl of assay buffer and then incubated with 150 µl of 20 ng/ml NP-BSA for 1 hr±10 minute in $CO_2$ incubator at 37° C. with 5% $CO_2$. After incubation, 50 µl of cell supernatant and 50 µl of 1 mM M-NAG substrate is added in 96 well black plate. The plate is incubated at 37° C. and 5% CO2 for 40 minutes. After incubation, 150 µl of cold sodium carbonate buffer is added. Florescence of plate is measured at Ex 360 nm and Ex 440 nm.

Relative accuracy and precision is analysed with different potency, six replicates for each level by two analyst for Beta hexosaminidase as per USP chapter 1033

Histamine Release Assay

Cell line: RBL2H3 hFCe R1A clone 7

β-hexosaminidase degranulation is performed on Day 1. β-hexosaminidase degranulation is performed on Day 2 and collected supernatant. 50 µl indicator buffer is added in all assay wells.

Which has different potency level 50 µl of different dose of reference standard and Sample at different potency levels i.e 60%, 80%, 100%, 125% and 156%. In 2 mL 96 well plate, 50 µl of each sample and/or controls and/or kit standards are added. 10 µl of Acylation reagent is added in all assay wells. The plate is covered and incubated for at least 30 minutes at room temperature. 1.8 mL of 1× assay buffer is added and mixed properly. In the microtiter plate, 50 µl of Acylated samples are added as per plate layout. 50 µl of freshly prepared 1× enzyme conjugate. 50 µl of histamine antiserum is added. Incubated at room temperature for at least 3 hours on at 500 rpm. 250 µl wash buffer is used to wash the plate 4 times. 100 µl of TMB substrate solution is added. 100 µl of TMB stop solution is added to stop the substrate reaction. Absorbance is measured at 450 nm wavelength within 15 minutes after adding stop solution.

Relative accuracy and precision is analysed with different potency, six replicates for each level by two analyst for Histamine Release assay as per USP chapter 1033

| Qualification Parameter | Beta Hex degranulation Assay (representative FIG. 4) | Histamine Release assay (representative FIG. 5) |
| --- | --- | --- |
| Precision | Maximum variation Intra plate is 10.40%. Maximum variation Inter plate is 8.18%. Overall % RSD is 8.72%. Maximum variation is 13.66%. | Maximum % RSD for Intra plate is 23.54%. Maximum % RSD for Inter plate is 16.24%. Overall % RSD is 9.79%. Maximum variation is 18.77%, |
| Accuracy | % Recovery at 64% is 103.4%. % Recovery of 80% is 100.8%. % Recovery of 100% is 102.7%. % Recovery of 125% is 103.9%. % Recovery of 156% is 99.5%. Each potency level is within 99.5-103.9%. | % Recovery at 64% is 93.2. % Recovery of 80% is 91.4. % Recovery of 100% is 97.2. % Recovery of 125% is 99.3. % Recovery of 156% is 96.8. Each potency level is within 70-130%. |

High variation in precision results to inconsistency in results for the determination of the potency while % recovery away from 100% leads to results inaccuracy in Potency.

Beta hex-degranulation assay is more precise as the variation is less in comparison to histamine release assay.

Further, Beta hex-degranulation assay recovery is around 100% makes it accurate as compared to histamine release assay.

Example 5

β-Hexosaminidase Degranulation Assay

Cell line: RBL2H3 hFCe R1A clone 7

96 well cell culture plate is seeded with 100 µl/well of cell suspension ($0.3 \times 10^6$ cells/ml) and incubated at 37° C.±0.5° C. and 5%±1% $CO_2$ for 4 hours. 50 µl of different dose of sample is mixed and 50 µl of 200 ng/mL of IgE is diluted. This mixture is incubated at RT for 1.5 hours. After incubation, 50 µl of drug-IgE mixture is transferred to cell containing plate and further this mixture is incubated for overnight (18 hours) in $CO_2$ incubator at 37° C. with 5% $CO_2$. After overnight incubation, cells are washed twice with 200 µl of assay buffer and then incubated with 150 µl of 5 µg/ml for 1 hr±10 minute in $CO_2$ incubator at 37° C. with 5% $CO_2$. After incubation, 50 µl of cell supernatant and 50 µl of 1 mM M-NAG substrate is added in 96 well black plate. The plate is incubated at 37° C. and 5% CO2 for 30 minutes. After incubation, 150 µl of cold sodium carbonate buffer is added. Florescence of plate is measured at Ex 360 nm and Ex 440 nm.

Omalizumab β-Hexosaminidase Degranulation Assay Procedure

Day 1
  Cell seeding in 96 well TC assay Plate (Plate 1 pre-seeded cell plate)
  Serial dilution of Test/Reference sample in deep well plate to vary anti-IgE concentration from higher to lower concentration (Plate 2)
  Incubation of diluted Test/Reference sample (anti-IgE) with anti-NP IgE in V-bottom plate (Plate 3 neutralization plate)
  Sensitization of cells and neutralization of antibody in plate 1 by incorporating mixture of anti-NP-IgE and anti-IgE from plate 3

Day 2
  Washing and Stimulation of cells with NP-BSA (Plate 1)
  Transfer of assay samples from plate 1 to new V-bottom plate (Plate 4)
  Detection of β-hexosaminidase activity in clear bottom black plate (Plate 5)
  Reading and Data analysis Anti-IgE antibody bioactivity is determined through β-hexosaminidase degranulation assay.

The invention claimed is:

1. An assay method comprising:
   a) seeding RBL 2H3 hFCεRIa cells in an assay plate with a MEM media to form a cell suspension, wherein the RBL 2H3 hFCεRIa cells comprise an hFCεRIa receptor with an IgE or an NP IgE and an anti-IgE antibody;
   b) optionally incubating the cell suspension with CO2,
   c) sensitising and neutralizing the RBL 2H3 cells;
   d) transferring the sensitized and neutralized RBL 2H3 cells obtained from step (c) to a pre-seeded assay plate;
   e) incubating the pre-seeded assay plate;
   f) washing the pre-seeded assay plate;
   g) mixing an antigen into the pre-seeded assay plate and incubating the pre-seeded assay plate to obtain a supernatant;
   h) transferring the supernatant obtained from the incubation in step (g) from the pre-seeded assay plate into a test assay plate;
   i) incorporating a substrate into the test assay plate and incubating the test assay plate; and
   j) measuring bioactivity of the anti-IgE antibody.

2. The assay method as claimed in claim 1, wherein the concentration of the anti-IgE antibody in step (c) is varying.

3. The assay method as claimed in claim 2, wherein the varying concentration of the anti-IgE antibody in step (c) is derived from the assay plate prepared with varying concentration from higher to lower concentration of the anti-IgE antibody with dilution in the MEM media.

4. The assay method as claimed in claim 1, wherein the concentration of the NP-IgE is constant and selected from a group consisting of about 30 µl, about 40 µl, about 50 µl, and about 60 µl.

5. The assay method as claimed in claim 1, wherein the anti-IgE antibody volume is constant in step (c) and is selected from the group consisting of about 30 µl, about 40 µl, about 50 µl, and about 60 µl.

6. The assay method as claimed in claim 1, wherein the incubation is performed in step from 18 hours, 19 hours, 20 hours, 21 hours, 22 hours, 23 hours, and 24 hours.

7. The assay method as claimed in claim 1, wherein temperature of the incubation in step (e) and/or step (g) is about 37° C.

8. The assay method as claimed in claim 1, wherein the washing of step (f) is performed one or two times with a Tyrode's buffer containing 1% BSA, phosphate buffer, and carbonate citrate.

9. The assay method as claimed in claim 1, wherein the antigen is selected from a group consisting of NP-BSA (bovine serum albumin) and anti-IgE antibody.

10. The assay method as claimed in claim 1, wherein the substrate is M-NAG.

11. The assay method as claimed in claim 10, wherein the M-NAG concentration is selected from a group consisting of about 0.5 mM, about 1 mM, about 1.5 mM, and about 2 mM.

12. The assay method as claimed in claim 1, wherein the substrate is incubated for about 30 minutes to 40 minutes at 37° C.

13. The assay method as claimed in claim 1, further comprising a quenching of the assay reaction post step (i) by using an ice cold sodium bicarbonate buffer.

14. The assay method as claimed in claim 1, wherein the bioactivity of the anti-IgE antibody is measured within 2 days.

15. The assay method as claimed in claim 1, wherein the bioactivity is measured by using an enzyme selected from a group consisting of prostaglandins, leukotrienes, kinins, ECF-A, PAF (platelet activating factor), histamine, and ß-hexosaminidase.

16. The assay method as claimed in claim 1, wherein the bioactivity of the anti-IgE antibody is measured by the B-hexosaminidase degranulation takes less time than a histamine release degranulation.

17. The assay method as claimed in claim 1, wherein the antigen in step (g) is incubated for at least 70 minutes.

18. The assay method as claimed in claim 12, wherein the substrate is incubated for about 30 minutes at 37° C.

19. The assay method as claimed in claim 15, wherein the bioactivity of the anti-IgE antibody is measured within 1.5 days.

* * * * *